(12) United States Patent
Sato et al.

(10) Patent No.: US 9,642,524 B2
(45) Date of Patent: May 9, 2017

(54) SLIT LAMP MICROSCOPE

(71) Applicant: KABUSHIKI KAISHA TOPCON, Itabashi-ku (JP)

(72) Inventors: Toshiaki Sato, Itabashi-ku (JP); Takanori Takeda, Shimotsuga-gun (JP); Takahiro Watanabe, Shinagawa-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 14/780,723

(22) PCT Filed: Mar. 19, 2014

(86) PCT No.: PCT/JP2014/057593
§ 371 (c)(1),
(2) Date: Sep. 28, 2015

(87) PCT Pub. No.: WO2014/156900
PCT Pub. Date: Oct. 2, 2014

(65) Prior Publication Data
US 2016/0051141 A1    Feb. 25, 2016

(30) Foreign Application Priority Data

Mar. 28, 2013  (JP) ................................. 2013-069567

(51) Int. Cl.
*A61B 3/10*  (2006.01)
*A61B 3/14*  (2006.01)
(Continued)

(52) U.S. Cl.
CPC ............ *A61B 3/135* (2013.01); *A61B 3/0075* (2013.01)

(58) Field of Classification Search
USPC ................................................ 351/200–246
See application file for complete search history.

(56) References Cited

U.S. PATENT DOCUMENTS

| | | | | |
|---|---|---|---|---|
| 4,877,321 | A | * 10/1989 | Ichihashi | ............... A61B 3/135 351/214 |
| 6,072,623 | A | * 6/2000 | Kitajima | ................ A61B 3/135 351/221 |
| 2014/0139807 | A1 | * 5/2014 | Uchiyama | .............. A61B 3/135 351/214 |

FOREIGN PATENT DOCUMENTS

JP         6 90905       4/1994
JP      2003 299619    10/2003
(Continued)

OTHER PUBLICATIONS

International Search Report Issued Jun. 10, 2014 in PCT/JP14/057593 Filed Mar. 19, 2014.

(Continued)

*Primary Examiner* — Mohammed Hasan
(74) *Attorney, Agent, or Firm* — Oblon, McClelland, Maier & Neustadt, L.L.P.

(57) ABSTRACT

Provided is a slit lamp microscope capable of controlling irradiation of slit light and background illumination light interlockingly. Embodiment includes a main illumination system, background illumination system, observation system and controller. The main illumination system includes a first light source unit that outputs first light and slit forming unit that forms a slit with changeable width, and illuminates an eye with the first light having passed through the slit. The background illumination system includes a second light source unit that outputs second light, and illuminates a peripheral area of an eye area irradiated with the first light. The observation system includes an eyepiece lens, imaging device, and group of optical elements that guides reflected light of the first light and reflected light of the second light from the eye to the eyepiece lens and imaging device. The controller interlockingly controls the main illumination system and second light source unit.

7 Claims, 8 Drawing Sheets

(51) Int. Cl.
   *A61B 3/135*    (2006.01)
   *A61B 3/00*     (2006.01)

(56)         References Cited

FOREIGN PATENT DOCUMENTS

JP        2012 228309      11/2012
JP        2012 254197      12/2012
WO    WO 2012/118010 A1    9/2012
WO        2012 172907      12/2012

OTHER PUBLICATIONS

Extended European Search Report issued Oct. 24, 2016 in European Application No. 14776267.8-1666/2979621 PCT/JP2014057593, 7 pages.

* cited by examiner

SLIT LAMP MICROSCOPE

FIELD OF THE INVENTION

The present invention relates to a slit lamp microscope.

BACKGROUND OF THE INVENTION

A slit lamp microscope is an ophthalmologic apparatus that uses slit light to cut an optical section of a cornea, thereby obtaining an image of a cross-section of the cornea. As disclosed in Patent Documents 1 and 2, a slit lamp includes a main illumination system for irradiating an eye with slit light and a background illumination system for illuminating an area around the slit light. Light irradiated to an eye by the background illumination system is referred to as background illumination light.

The background illumination system is configured as an optical system that guides light output from a light source in the main illumination system. Therefore, it is difficult to control irradiation of slit light and irradiation of background illumination light independently from each other, and also difficult to link the control of irradiation of slit light with the control of irradiation of background illumination light.

PRIOR ART DOCUMENTS

Patent Documents

[Patent Document 1] Japanese Published Unexamined Application H06-90905
[Patent Document 2] Japanese Published Unexamined Application 2003-299619

SUMMARY OF THE INVENTION

Problem to be Solved by the Invention

The present invention is achieved to solve the aforementioned problem and a purpose thereof is to provide a slit lamp microscope that is capable of controlling irradiation of slit light and background illumination light interlockingly.

Means for Solving the Problem

A slit lamp microscope of an embodiment includes: a main illumination system that includes a first light source unit that outputs first light and a slit forming unit that forms a slit with changeable width, and illuminates an eye with the first light having passed through the slit; a background illumination system that includes a second light source unit that outputs second light, and illuminates, with the second light, a peripheral area of an area of the eye irradiated with the first light; an observation system that includes an eyepiece lens, an imaging device, and a group of optical elements that guides reflected light of the first light and reflected light of the second light from the eye to the eyepiece lens and the imaging device; and a controller that interlockingly controls the main illumination system and the second light source unit.

Effect of the Invention

According to the present invention, it is possible to link control of irradiation of slit light and background illumination light with each other.

DETAILED DESCRIPTION

Examples of embodiments of slit lamp microscopes related to the present invention are explained in detail with reference to the diagrams. Note that contents of the documents cited in the specification may be incorporated as contents of the embodiments below.

First, directions are defined. The direction from a lens (objective lens) arranged closest to the subject side in a device optical system is a "front direction", while the direction opposite thereto is a "rear direction". Moreover, the horizontal direction orthogonal to the front direction is a "left-right direction". Further, the direction orthogonal to both the front-rear direction and the left-right direction is a "vertical direction (upward-downward direction)".

[Exterior Configuration]

Figure 1:
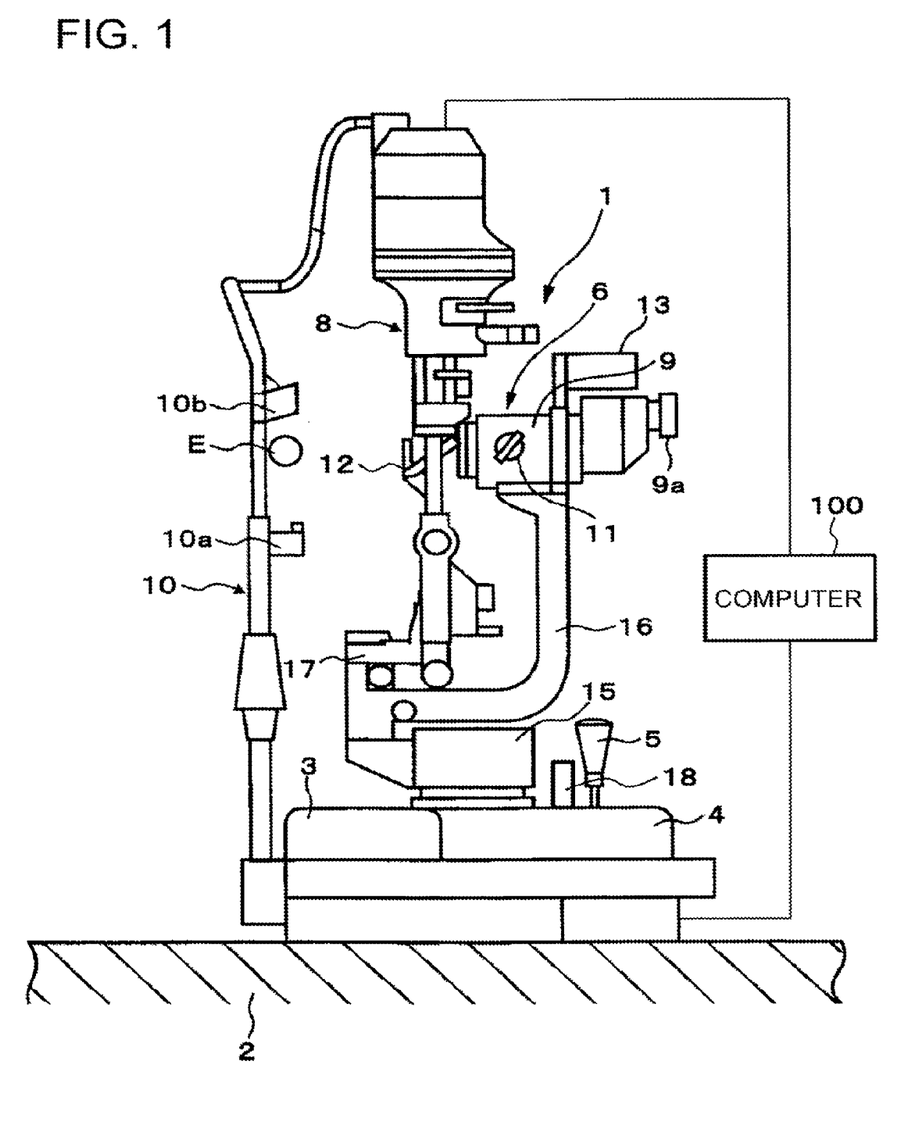
FIG. 1 is a schematic diagram illustrating an example of the configuration of a slit lamp microscope according to an embodiment.

The exterior configuration of a slit lamp microscope related to the present embodiment is explained with reference to FIG. 1. A computer 100 is connected to a slit lamp microscope 1. The computer 100 performs various control processing and arithmetic processing. Instead of providing the computer 100 separate from a main body of the microscope (a case that houses optical systems etc.), a similar computer may be arranged inside the main body of the microscope.

The slit lamp microscope 1 is placed on a table 2. Incidentally, the computer 100 may be arranged on another table or other locations. A base 4 is configured to be movable in the horizontal direction via a moving mechanism 3. The base 4 is moved by tilting operations of an operation handle 5.

A supporting part 15 that supports an observation system 6 and an illumination system 8 is provided on the top surface of the base 4. Further, the supporting part 15 supports a background illumination system 20 illustrated in FIG. 2. A supporting arm 16 that supports the observation system 6 is provided on the supporting part 15 such that it is rotatable in the left-right direction. A supporting arm 17 that supports the illumination system 8 and the background illumination system 20 is provided on the top part of the supporting arm 16 such that it is rotatable in the left-right direction. The supporting arms 16 and 17 are independently rotatable around the same axis.

The observation system 6 is moved by turning the supporting arm 16 by hand. The illumination system 8 and the background illumination system 20 are moved by turning the supporting arm 17 by hand. A configuration may be adopted in which each of the supporting arms 16 and 17 is rotated by an electric mechanism. In such a case, an actuator that generates driving forces for turning the respective supporting arms 16 and 17 and a transmission mechanism that transmits the driving forces are provided. The actuator is configured by, for example, a stepping motor (pulse motor). The transmission mechanism is configured by, for example, a combination of gearwheels or rack and pinion, etc.

The illumination system 8 irradiates an eye E with illumination light. As mentioned above, the illumination system 8 may be swung in the left-right direction around a rotation axis. Thereby, it becomes possible to change the direction of irradiation of the illumination light with respect to the eye E. The illumination system 8 may be configured such that it is allowed to be swung vertically. That is, it may be configured such that the angle of elevation and the angle of depression of the illumination light can be changed.

An illumination intensity operating part 18 provided on the base 4 is used for changing the intensity of the illumination light. The illumination intensity operating part 18 may also be used for the intensity of background illumination light irradiated to the eye E by the background illumination system 20. Further, other members may be used for changing the intensity of the illumination light and that of the background illumination light. Examples of such other members include operating members provided on the case of the slit lamp microscope 1 and operating members provided in the computer 100.

The observation system 6 includes a pair of left and right optical systems that guides reflected light of the illumination light (and the background illumination light) from the eye E. These optical systems are housed within a lens tube body 9. The terminal of the lens tube body 9 is an eyepiece 9a. The examiner observes the eye E through the eyepiece 9a. As mentioned above, the lens tube body 9 may be rotated in the left-right direction by turning the supporting arm 16. Thereby, the direction of the observation system 6 with respect to the eye E is changed. Note that the reflected light of the illumination light includes a variety of light components passing the eye E such as scattered light, and light including such a variety of light components is collectively referred to as "reflected light."

A face holder 10 is provided in a position facing the lens tube body 9. The face holder 10 is provided with a jaw holder 10a and a forehead supporter 10b for stably placing the subject's face.

An observation magnification operating knob 11 for changing observation magnification is provided on the side surface of the lens tube body 9. Further, an imaging device 13 for photographing the eye E is attached to the lens tube body 9. The imaging device 13 includes an image sensor. The image sensor is a photoelectric transducer that detects light and outputs electric signals (image signals). The image signals are input into the computer 100. The image sensor is, for example, a CCD (Charge Coupled Device) image sensor or a CMOS (Complementary Metal Oxide Semiconductor) image sensor. A mirror 12 that reflects illumination light beam output from the illumination system 8 towards the eye E is provided in a lower position of the illumination system 8. Further, the mirror 12 reflects background illumination light output from the background illumination system 20 towards the eye E.

[Configurations of Optical Systems]

Figure 2:
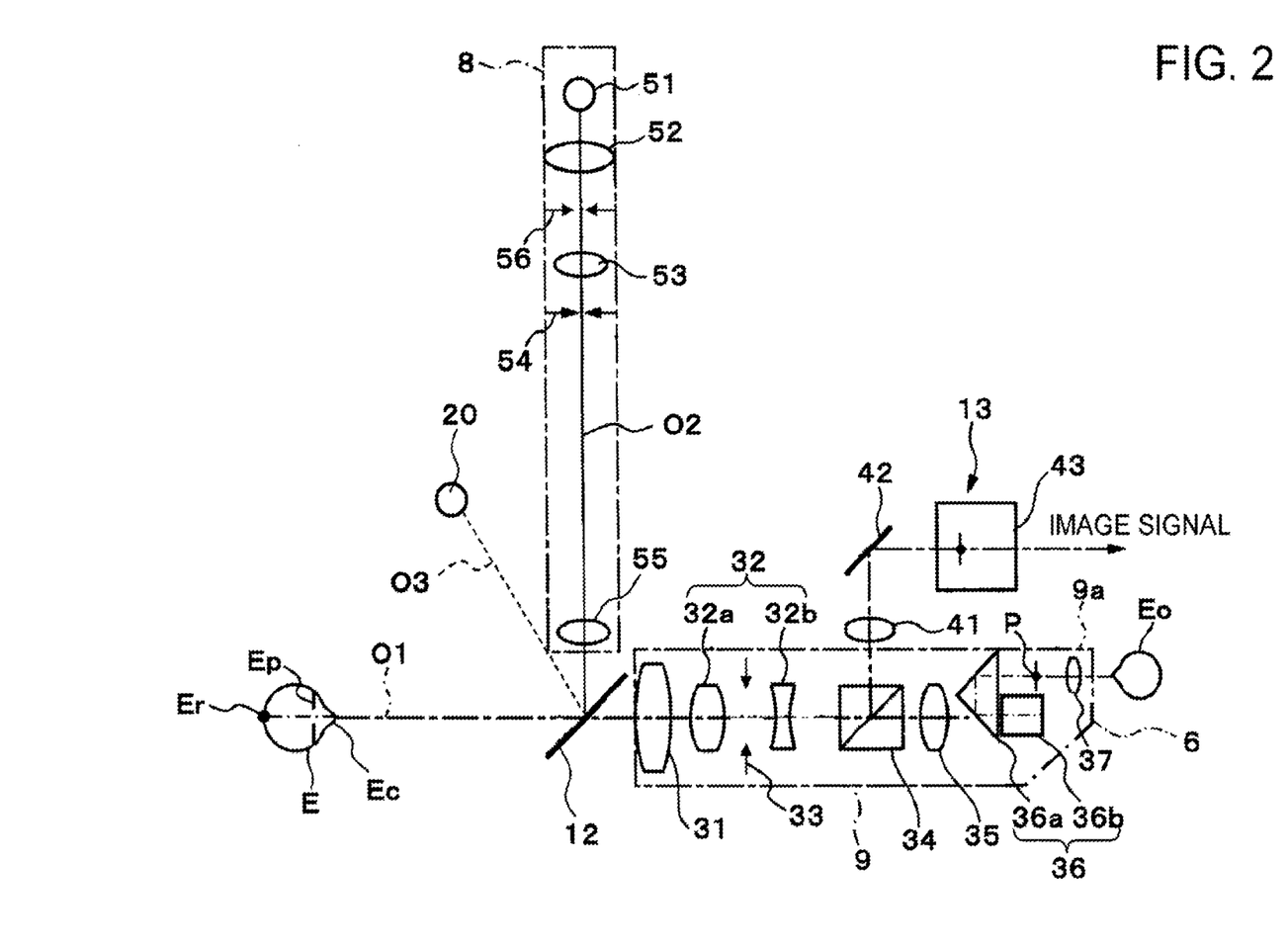
FIG. 2 is a schematic diagram illustrating an example of the configuration of a slit lamp microscope according to an embodiment.

A configuration of optical systems of the slit lamp microscope 1 is described with reference to FIG. 2. The slit lamp microscope 1 includes the observation system 6, the illumination system 8, and the background illumination system 20.

[Observation System]

The observation system 6 includes a pair of left and right optical systems. The left and right optical systems have substantially the same configuration. By means of the left and right optical systems, the examiner is capable of observing the eye E with both eyes. Note that FIG. 2 illustrates only one of the left and right optical systems of the observation system 6. The symbol O1 indicates an optical axis (observation optical axis) of the observation system 6.

Each of the left and right optical systems of the observation system 6 includes an objective lens 31, a magnification optical system 32, a diaphragm 33, a relay lens 35, a prism 36, and an eyepiece lens 37. A beam splitter 34 is provided to one or both of the left and right optical systems. The eyepiece lens 37 is provided inside the eyepiece 9a. The symbol P indicates an image-formation position of light guided towards the eyepiece lens 37. The symbol Ec indicates the cornea of the eye E, the symbol Ep indicates the iris, and the symbol Er indicates the fundus. The symbol Eo indicates the examiner's eye.

The magnification optical system 32 includes a plurality of (for example, two) magnifying lenses 32a and 32b. In the present embodiment, a plurality of magnifying lens groups is provided such that they are selectively insertable in the optical path of the observation system 6. The magnifying lens groups give different magnifying powers from each other. A magnifying lens group arranged in the optical path of the observation system 6 functions as the magnifying lenses 32a and 32b. With this, magnifications (angle of view) of observation images and photographed images of the eye E are varied. Varying magnification (that is, switching of the magnifying lens groups arranged in the optical path of the observation system 6) is performed by operating the observation magnification operating knob 11. Moreover, magnification may be varied electrically by using a switch (not illustrated) etc.

The beam splitter 34 divides the light travelling along the observation optical axis O1 into two. Light penetrated the beam splitter 34 is guided to the examiner's eye Eo via the relay lens 35, the prism 36, and the eyepiece lens 37. The prism 36 includes two optical elements 36a and 36b, and parallelly translates the travelling direction of the light upwards.

Meanwhile, light reflected by the beam splitter 34 is guided to an image sensor 43 of the imaging device 13 via the relay lens 41 and the mirror 42. The image sensor 43 detects this reflected light to Generate image signals.

[Illumination System]

The illumination system 8 includes a light source 51, a relay lens 52, an illumination diaphragm 56, a condensing lens 53, a slit forming unit 54, and a condensing lens 55. The symbol O2 indicates an optical axis (illumination optical axis) of the illumination system 8.

The light source 51 outputs illumination light. Note that the illumination system 8 may be provided with a plurality of light sources. For example, both a light source outputting continuous light (halogen lamp, LED, etc.) and a light source outputting flash light (xenon lamp, LED, etc.) may be provided as the light source 51. Moreover, a light source for cornea observation and a light source for eye-fundus observation may be separately provided. The light source 51 includes at least a visible light source that outputs visible light.

The slit forming unit 54 is used for generating slit light. The slit forming unit 54 includes a pair of slit blades. The width of the slit light is varied by changing the distance between the slit blades (slit width).

The size of a light-transmitting part of the illumination diaphragm 56 may be varied. The illumination diaphragm 56 is particularly effective for eye-fundus observation. For example, the illumination diaphragm 56 is used for reducing reflection of the illumination light by the cornea Ec, crystalline lens, etc. and adjusting the brightness of the illumination light.

[Background Illumination System]

The background illumination system 20 irradiates the eye with background illumination light. The background illumination light is irradiated on a peripheral area of an area on which the illumination light is irradiated by the illumination system 8. Here, it is sufficient that an irradiation area of the background illumination light includes at least the peripheral area. For example, an irradiation area of the background illumination light may be overlapped with at least part of an area illuminated by the illumination system 8.

The background illumination system 20 includes a light source (background light source). The background light source includes at least a visible light source that outputs visible light. The visible light is used for observation and photography. The background light source may include an infrared light source that outputs infrared light. The infrared light is used for observation and photography of meibomian glands, for example. If the background illumination system 20 includes both the visible light source and the infrared light source, these light sources are selectively used, for example. The background illumination system 20 may include one or more lenses for focusing light output from the background light source. The symbol O3 indicates an optical axis (background illumination optical axis) of the background illumination system 20.

Light output from the background light source is reflected by the mirror 12 and irradiated on the eye E (after focused by the aforementioned lenses). An irradiation area of the background light source includes a peripheral area of an area illuminated by the illumination system 8.

[Configuration of Control System]

A control system of the slit lamp microscope 1 is explained with reference to FIG. 3. The control system of the slit lamp microscope 1 is configured with a controller 101 as the center. At least part of configuration of the control system may be included in the computer 100.

[Controller]

The controller 101 controls each part of the slit lamp microscope 1. The controller 101 performs control of the observation system 6, control of the illumination system 8, and control of the background illumination system 20. The control of the observation system 6 includes control of the magnification optical system 32, control of the diaphragm 33, and control of charge accumulation time, sensitivity, frame rate, etc. of the image sensor 43. The control of the illumination system 8 includes control of the light source 51, control of the slit forming unit 54, control of the illumination diaphragm 56, and the like. The control of the background illumination system 20 includes control of the background light source. In an example illustrated in FIG. 3, a visible background light source 20a that outputs visible light and an infrared background light source 20b that outputs infrared light are provided as the background light source; however, only one of these (for example, the visible background light source) may be provided.

The controller 101 includes a microprocessor, RAM, ROM, hard disk drive, etc. Control programs are stored in advance in storage devices such as the ROM and the hard disk drive. Operations of the controller 101 are realized by cooperation of the control programs and the hardware. The controller 101 is arranged in the main body (for example, inside the base 4) of the slit lamp microscope 1 and/or the computer 100.

[Display]

The display 102 is controlled by the controller 101 to display a variety of information. The display 102 includes a display device such as a flat panel display (LCD etc.) or the like. The display 102 may be provided on the main body of the slit lamp microscope 1 or in the computer 100.

[Operating Unit]

The operating unit 103 includes an operating device and/or an inputting device. The operating unit 103 includes buttons and switches provided on the main body (such as the operation handle 5, the illumination intensity operating part 18, etc.) and operating devices of the computer 100 (a mouse, a keyboard, etc.). Moreover, the operating unit 103 may include arbitrary operating devices and inputting devices such as a trackball, operation panel, switch, button, dial, etc.

Figure 3:
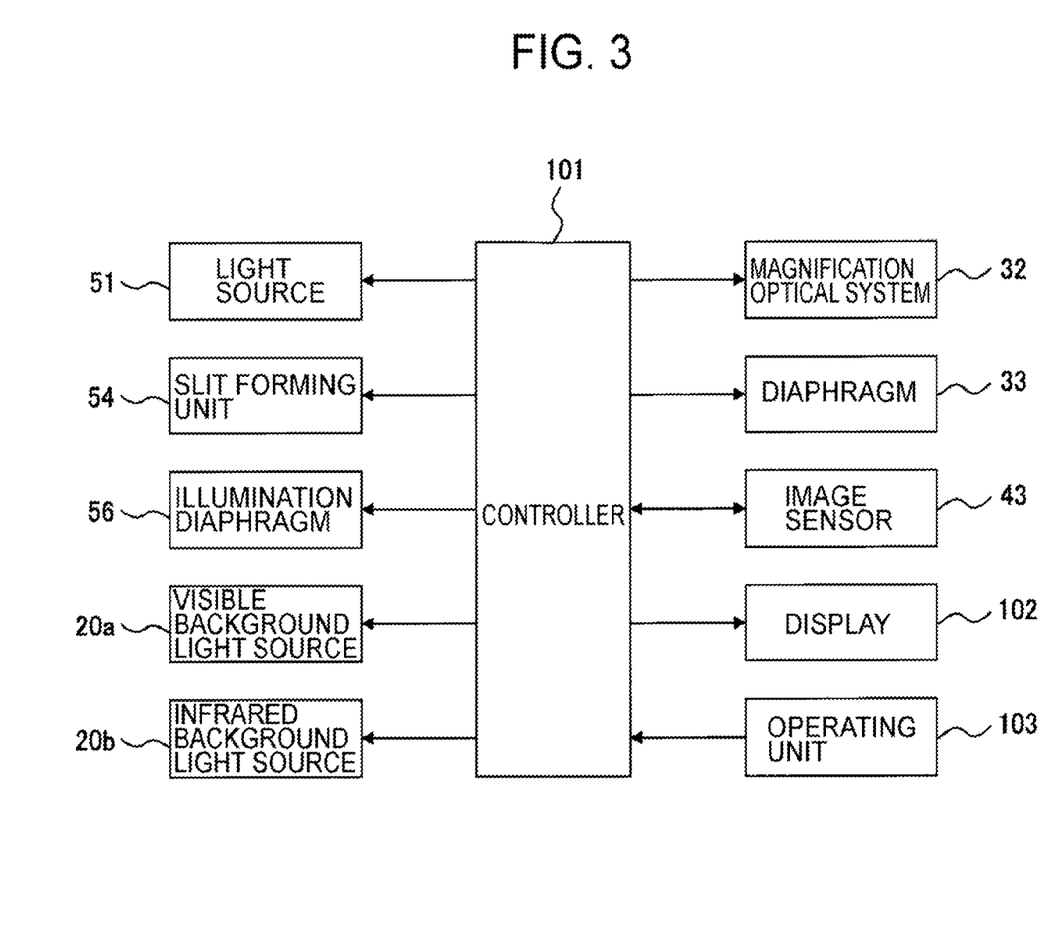
FIG. 3 is a schematic diagram illustrating an example of the configuration of a slit lamp microscope according to an embodiment.

In FIG. 3, the display 102 and the operating unit 103 are illustrated separately; however, at least part of them may be integrally configured. As a detailed example thereof, a touch screen may be applied.

[Operations]

Operations of the slit lamp microscope 1 are explained.

Figure 4:
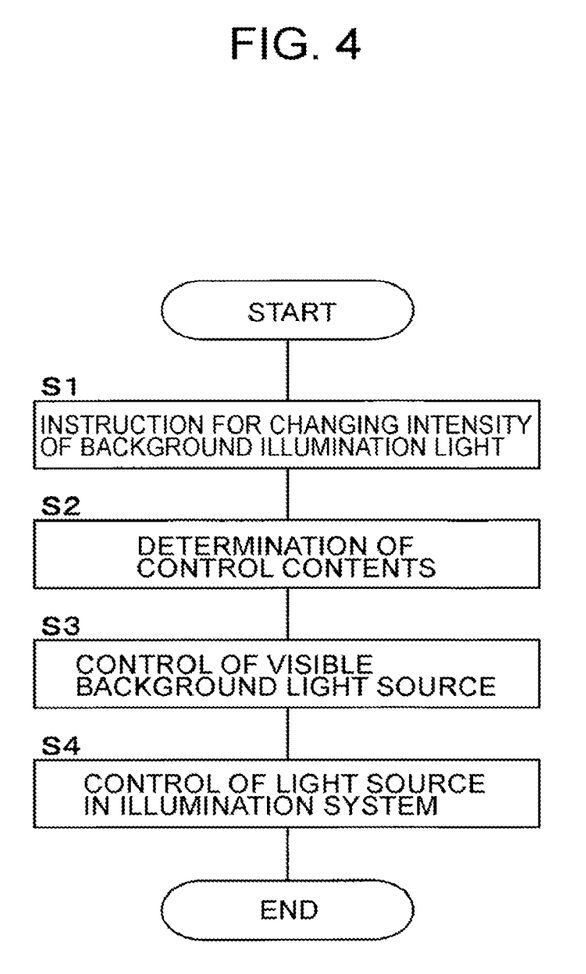
FIG. 4 is a flow chart illustrating an example of an operation of a slit lamp microscope according to an embodiment.
Figure 5:
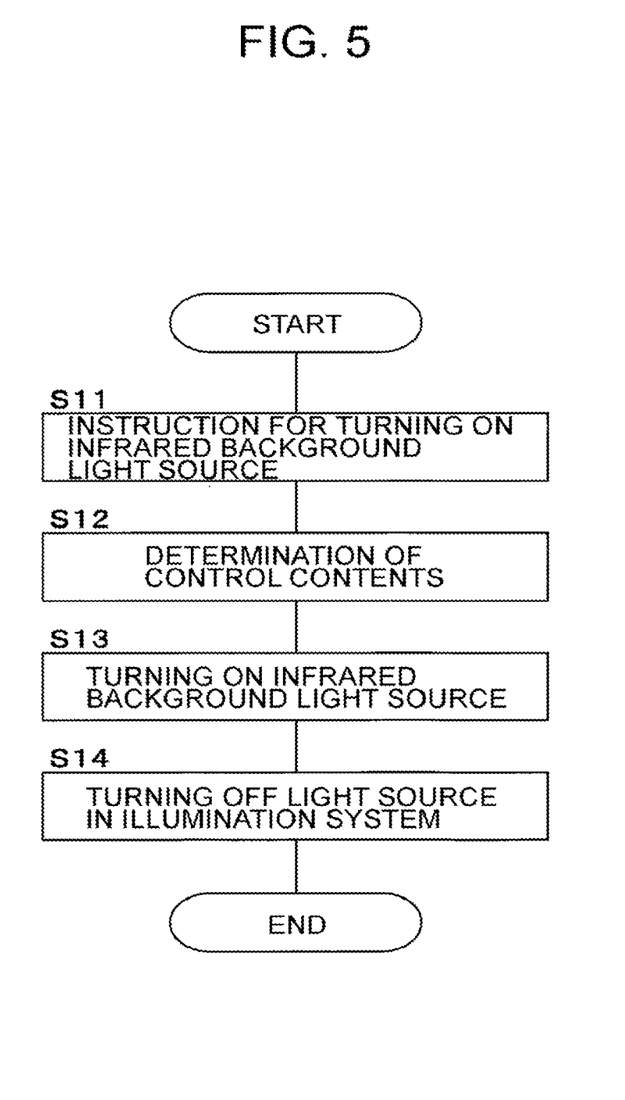
FIG. 5 is a flow chart illustrating an example of an operation of a slit lamp microscope according to an embodiment.

Examples of operations of the slit lamp microscope 1 are illustrated in FIGS. 4 to 9. The operational example illustrated in FIG. 4 is an example of a preset process for associating slit width (interval information) to the slit width specifying buttons. The operational example illustrated in FIG. 5 is an example of a slit width reproduction process for reproducing the preset slit width.

Figure 6:
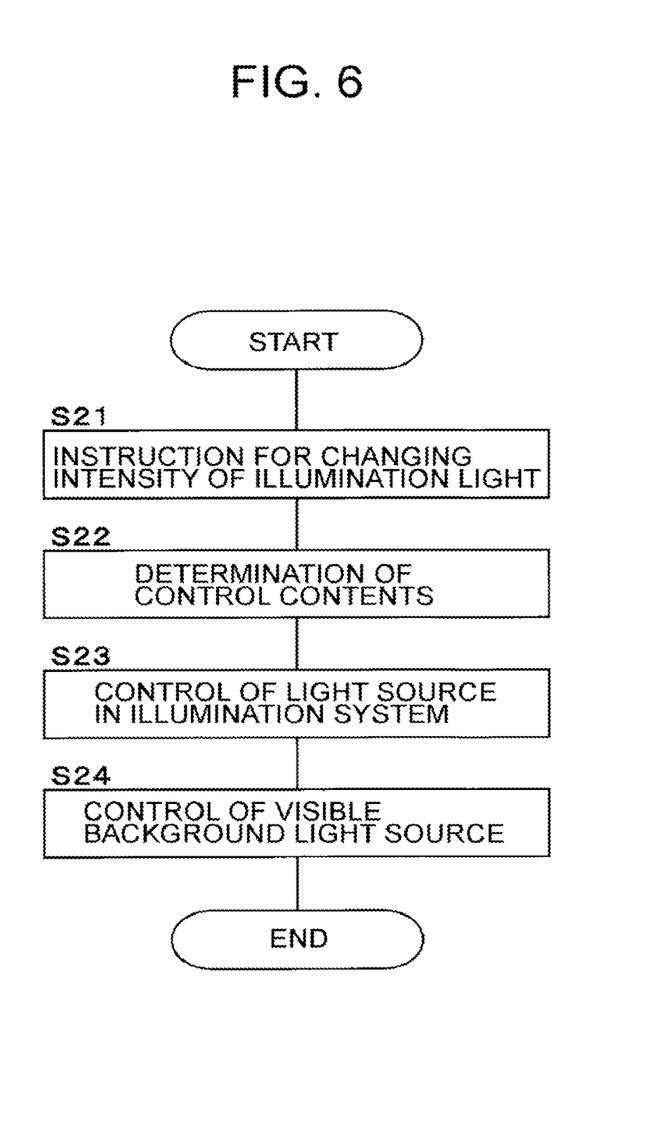
FIG. 6 is a flow chart illustrating an example of an operation of a slit lamp microscope according to an embodiment.

With the first to third operational examples shown in FIGS. 4 to 6, cases are explains in which control of the light source 51 of the illumination system 8 and control of the background light source of the background illumination system 20 are linked with each other. More specifically, the first and second operational examples correspond to cases in which the light source 51 and the background light source are interlockingly controlled according to a control instruction to the background light source. On the other hand, the third operational example corresponds to a case in which the light source 51 and the background light source are interlockingly controlled according to a control instruction to the light source 51.

Figure 7:
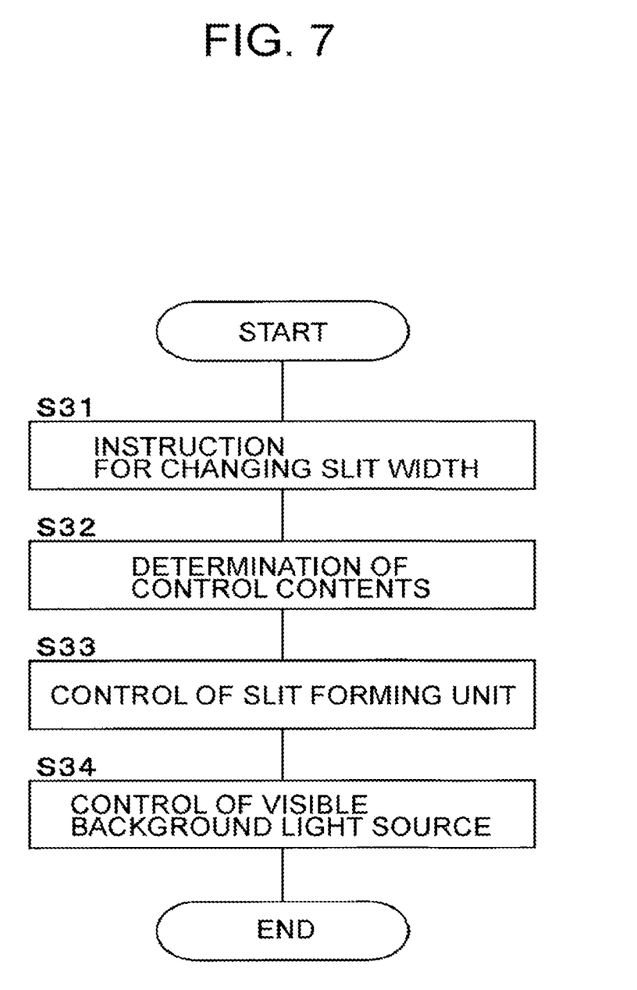
FIG. 7 is a flow chart illustrating an example of an operation of a slit lamp microscope according to an embodiment.
Figure 8:
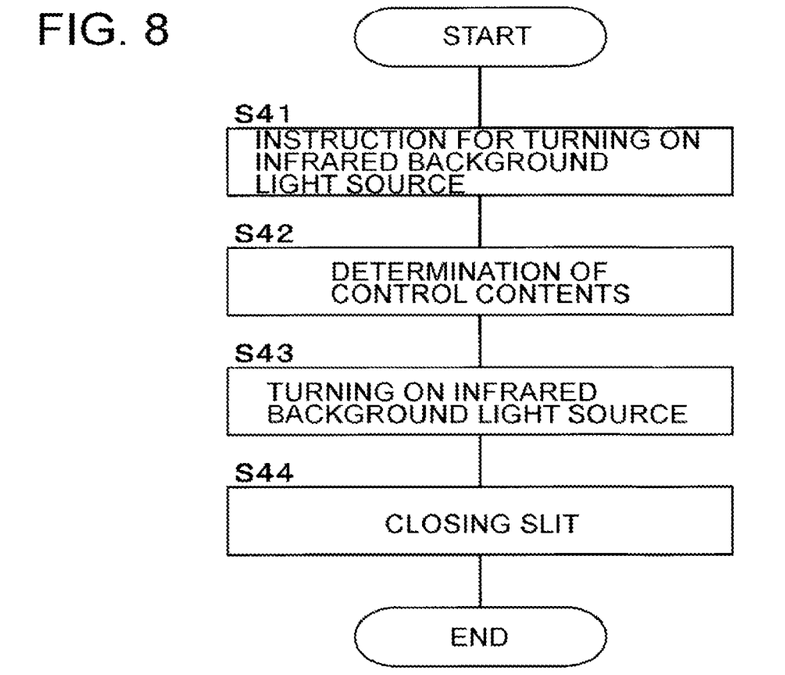
FIG. 8 is a flow chart illustrating an example of an operation of a slit lamp microscope according to an embodiment.

The fourth and fifth operational examples shown in FIGS. 7 and 8, cases are explains in which control of the slit forming unit 54 of the illumination system 8 and control of the background light source of the background illumination system 20 are linked with each other. More specifically, the fourth operational example corresponds to a case in which the slit forming unit 54 and the background light source are interlockingly controlled according to a control instruction to the slit forming unit 54. On the other hand, the fifth operational example corresponds to a case in which the slit forming unit 54 and the background light source are interlockingly controlled according to a control instruction to the background light source.

Figure 9:
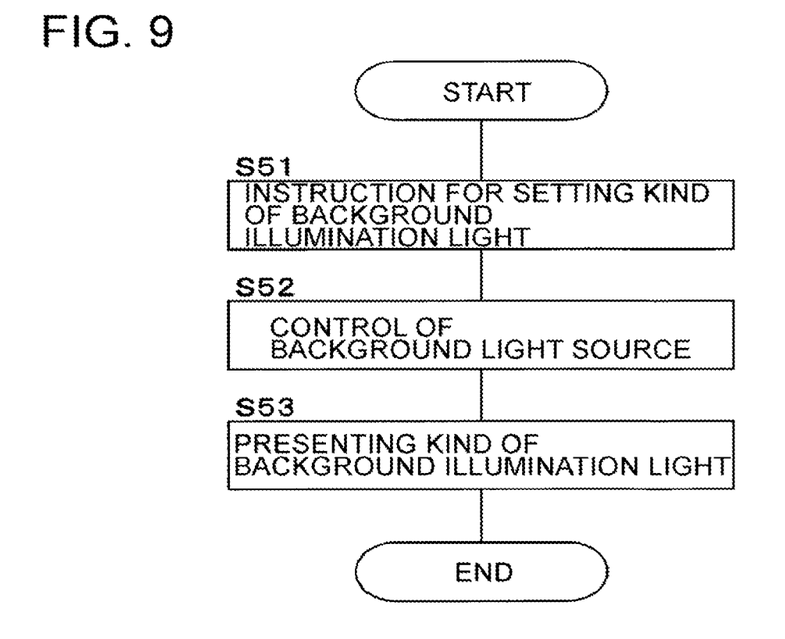
FIG. 9 is a flow chart illustrating an example of an operation of a slit lamp microscope according to an embodiment.

The sixth operational example shown in FIG. 9 is applicable to cases in which the both visible background light source and the infrared background light source are provided in the background illumination system 20.

Here, a control instruction means an operation for inputting control contents for components to be controlled (the light source 51, the background light source, the slit forming unit 54). The control instruction is performed manually and automatically. A manual control instruction is performed by using the operating unit 103.

As an example of an automatic control instruction, when the order of examinations is predetermined such as a case in which a clinical path is applied, it is possible to perform an automatic control instruction at the time of transition from one examination to another.

Another example of the automatic control instruction is a method on the basis of a photographed image acquired by the imaging device 13. In a specific example, the controller 101 is provided with: an illumination condition specifying unit that analyzes pixel values of a photographed image to specify an illumination condition; and a control content determining part that determines control contents based on the illumination condition specified. Examples of the illumination condition include intensity of illumination light, slit width, intensity of background illumination light, and the like. Further, examples of the illumination condition may include a relative relationship (large/small, degree, etc.) between intensity of illumination light (or slit width) and intensity of background illumination light. Illumination conditions are not limited to these; however, it is sufficient that an illumination condition indicates a state of illumination of the eye E. If such a configuration is adopted, a storage device stores in advance association information in which illumination conditions and control contents are associated with each other. The storage device is provided in the controller 101. The association information is created, for example, by attempting a variety of illumination conditions and control contents by use of a model eye or a living eye, or by performing theoretical simulation. Taken together, with such configurations, the illumination condition specifying unit analyzes a photographed image to specify an illumination condition, the control content determining part determines control contents corresponding to the specified illumination condition based on the association information, and the controller 101 performs control based on the determined control contents. Note that aspects of control based on an automatic control instruction are not limited to the above.

Interlocking control indicates execution of controls of two or more components in response to a single control instruction. The first to sixth operational examples are explained in the following. It is assumed that operations and processing to be performed before the operational examples have already been performed.

[First Operational Example: FIG. 4]

The first operational example explains a case in which the light source 51 and the background light source are interlockingly controlled in response to a control instruction to the background light source. This operational example is applied to a case in which both the light source 51 and the background light source are visible light sources. In other words, if this operational example is adopted, the infrared background light source 20b is not necessary.

Further, if this operational example is adopted, the storage device in the controller 101 stores in advance association information in which control contents for the visible background light source 20a and control contents for the light source 51 are associated with each other. In this association information, current values and/or voltage values applied to the visible background light source 20a and current values and/or voltage values applied to the light source 51 are associated with each other, for example. The association information is created, for example, by attempting a variety of control contents by use of a model eye or a living eye, or by performing theoretical simulation. The current values and/or voltage values included in the association information are determined according to properties and characteristics of light sources (constant voltage control, constant current control, luminous efficiency, emission spectrum, etc.). Association information in other operational examples may be created in similar ways.

(Step 1: Instruction for Changing Intensity of Background Illumination Light)

As a control instruction, an instruction is issued for changing intensity of light output from the visible background light source 20a (background illumination light). This control instruction is issued by use of the operating unit 103 or by the controller 101.

(Step 2: Determination of Control Contents)

The controller 101 refers to the association information to determine control contents corresponding to the control instruction input in Step 1. In this operational example, control contents (current values and/or voltage values) for the light source 51 and control contents (current values and/or voltage values) for the visible background light source 20a are determined based on contents of change in intensity of the background illumination light that is visible light.

(Step 3: Control of Visible Background Light Source)

The controller 101 controls the visible background light source 20a based on the control contents determined in Step 2. With this, intensity of the background illumination light output from the visible background light source 20a is varied by a change amount according to the control instruction.

(Step 4: Control of Light Source in Illumination System)

The controller 101 controls the light source 51 based on the control contents determined in Step 2. With this, intensity of the illumination light output from the light source 51 is varied by a change amount according to the amount of change in the intensity of the background illumination light.

Timing of execution of Step 3 and that of Step 4 are arbitrary. For example, the controller 101 is capable of performing one of Steps 3 and 4 after performing the other. Alternatively, the controller 101 is capable of performing Steps 3 and 4 in parallel.

[Second Operational Example: FIG. 4]

The second operational example explains a case in which the light source 51 and the background light source are interlockingly controlled in response to a control instruction to the background light source. This operational example is applied to a case in which the light source 51 is a visible light source and the background light source includes both a visible background light source and an infrared background light source.

If this operational example is adopted, the storage device in the controller 101 stores in advance association information in which control contents for the background light sources and control contents for the light source 51 are associated with each other. In this association information, kinds of the background light source to be used (the visible background light source 20a, the infrared background light source 20*b*) and use/non-use of the light source 51 are associated with each other, for example. The association information of the present operational example associates the infrared background light source 20*b* as a kind of the background light source to be used with non-use of the light source 51 that is a visible light source. In addition, the association information associates the visible background light source 20*a* as a kind of the background light source to be used with use of the light source 51, and further with intensities of output light therefrom (current values and/or voltage values).

(Step 11: Instruction for Turning on Infrared Background Light Source)

As a control instruction, an instruction is issued for turning on the infrared background light source 20*b*. This control instruction is issued by use of the operating unit 103 or by the controller 101. This control instruction is an instruction for switching from one state in which the visible background light source 20*a* is turned on to another state in which the infrared background light source 20*b* is turned on, or an instruction for switching from one state in which no background light source is turned on to another state in which the infrared background light source 20*b* is turned on.

(Step 12: Determination of Control Contents)

The controller 101 refers to the association information to determine control contents corresponding to the control instruction input in Step 1 (for turning on the infrared background light source 20*b*). The control contents determined is non-use of the light source 51. Non-use of the light source 51 means turning off of the light source 51 if the light source 51 is turned on, or maintaining a state in which the light source 51 is turned off.

(Step 13: Turning on Infrared Background Light Source)

The controller 101 turns on the infrared background light source 20*b* based on the control contents determined in Step 12. With this, the eye E is irradiated with background illumination light containing infrared light. If the control instruction is issued in the Step 11 when the visible background light source 20*a* is turned on, the controller 101 turns off the visible background light source 20*a*.

(Step 14: Turning Off Light Source in Illumination System)

If the control instruction is issued in the Step 11 when the light source 51 is turned off, Step 14 is not necessary. On the other hand, if the control instruction is issued in the Step 11 when the light source 51 is turned on, the controller 101 turns off the light source 51 based on the control contents determined in Step 12. Note that if Step 14 is performed, timing of execution of Step 13 and that of Step 14 are arbitrary.

[Third Operational Example: FIG. 6]

The third operational example explains a case in which the light source 51 and the background light source are interlockingly controlled in response to a control instruction to the light source 51. This operational example is applied to a case in which the light source 51 is a visible light source and the background light source includes a visible background light source.

Further, if this operational example is adopted, the storage device in the controller 101 stores in advance association information in which control contents for the light source 51 and control contents for the visible background light source 20*a* are associated with each other. In this association information, current values and/or voltage values applied to the light source 51 and current values and/or voltage values applied to the visible background light source 20*a* are associated with each other, for example.

(Step 21: Instruction for Changing Intensity of Illumination Light)

As a control instruction, an instruction is issued for changing intensity of light output from the light source 51 (illumination light). This control instruction is issued by use of the operating unit 103 or by the controller 101.

(Step 22: Determination of Control Contents)

The controller 101 refers to the association information to determine control contents corresponding to the control instruction input in Step 21. In this operational example, control contents (current values and/or voltage values) for the light source 51 and control contents (current values and/or voltage values) for the visible background light source 20*a* are determined based on contents of change in intensity of the illumination light that is visible light.

(Step 23: Control of Light Source in Illumination System)

The controller 101 controls the light source 51 based on the control contents determined in Step 22. With this, intensity of the illumination light output from the light source 51 is varied by a change amount according to the control instruction.

(Step 24: Control of Visible Background Light Source)

The controller 101 controls the visible background light source 20*a* based on the control contents determined in Step 22. With this, intensity of the background illumination light output from the visible background light source 20*a* is varied by a change amount according to the amount of change in the intensity of the illumination light. Note that timing of execution of Step 23 and that of Step 24 are arbitrary.

[Fourth Operational Example: FIG. 7]

The fourth operational example explains a case in which the slit forming unit 54 and the background light source are interlockingly controlled in response to a control instruction to the slit forming unit 54. This operational example is applied to a case in which the light source 51 is a visible light source and the background light source includes a visible background light source.

If this operational example is adopted, the storage device in the controller 101 stores in advance association information in which control contents for the slit forming unit 54 and control contents for the visible background light source 20*a* are associated with each other. In this association information, values of the slit width and current values and/or voltage values applied to the visible background light source 20*a* are associated with each other, for example. Alternatively, a threshold of the slit width may be recorded in this association information.

(Step 31: Instruction for Changing Slit Width)

As a control instruction, an instruction is issued for changing the width of the slit formed by the slit forming unit 54. This control instruction is issued by use of the operating unit 103 or by the controller 101.

(Step 32: Determination of Control Contents)

The controller 101 refers to the association information to determine control contents corresponding to the control instruction input in Step 31. In this operational example, control contents for the slit forming unit 54 and control contents (current values and/or voltage values) for the visible background light source 20*a* are determined based on contents of change in slit width. If the actuator in the slit forming unit 54 is a pulse motor, the control contents for the slit forming unit 54 is the number of pulses transmitted to the pulse motor.

As an example of processing in a case in which a threshold of the slit width is included in the association information, the controller 101 judges whether the slit width indicated by the control instruction is equal to or larger than the threshold. If it is judged that the slit width is equal to or larger than the threshold, the controller 101 determines that the slit width is increased to the value indicated by the control instruction for the control contents for the slit forming unit 54 and determines that the visible background light source 20*a* is turned off (that is, current value=0, voltage value=0) for the control contents for the visible background light source 20*a*.

(Step 33: Control of Slit Forming Unit)

The controller 101 controls the slit forming unit 54 based on the control contents determined in Step 32. With this, the slit width is varied by a change amount according to the control instruction.

(Step 34: Control of Visible Background Light Source)

The controller 101 controls the visible background light source 20*a* based on the control contents determined in Step 32. With this, intensity of the background illumination light output from the visible background light source 20*a* is varied by a change amount according to the amount of change in the slit width. Note that timing of execution of Step 33 and that of Step 34 are arbitrary.

[Fifth Operational Example: FIG. 8]

The fifth operational example explains a case in which the slit forming unit 54 and the background light source are interlockingly controlled in response to a control instruction to the background light source. This operational example is applied to a case in which the light source 51 is a visible light source and the background light source includes both a visible background light source and an infrared background light source.

If this operational example is adopted, the storage device in the controller 101 stores in advance association information in which control contents for the background light source and control contents for the slit forming unit 54 are associated with each other. In this association information, kinds of the background light source to be used (the visible background light source 20*a*, the infrared background light source 20*b*) and values of the slit width are associated with each other, for example. The association information of the present operational example associates the infrared background light source 20*b* as a kind of the background light source to be used with closure of the slit (that is, setting the slit width to zero).

(Step 41: Instruction for Turning on Infrared Background Light Source)

As a control instruction, an instruction is issued for turning on the infrared background light source 20*b*. This control instruction is issued by use of the operating unit 103 or by the controller 101. This control instruction is an instruction for switching from one state in which the visible background light source 20*a* is turned on to another state in which the infrared background light source 20*b* is turned on, or an instruction for switching from one state in which no background light source is turned on to another state in which the infrared background light source 20*b* is turned on.

(Step 42: Determination of Control Contents)

The controller 101 refers to the association information to determine control contents corresponding to the control instruction input in Step 41 (for turning on the infrared background light source 20*b*). The control contents determined is to set the slit width to zero. Setting the slit width to zero means changing the slit width from nonzero to zero, or maintaining a state in which the slit width is zero.

(Step 43: Turning on Infrared Background Light Source)

The controller 101 turns on the infrared background light source 20*b* based on the control contents determined in Step 42. With this, the eye E is irradiated with background illumination light containing infrared light. Note that if the control instruction of Step 41 is issued when the visible background light source 20*a* is being turned on, the controller 101 turns off the visible background light source 20*a*.

(Step 44: Closing Slit)

If the control instruction is issued in the Step 41 when the slit width is zero, Step 44 is not necessary. On the other hand, if the control instruction is issued in the Step 41 when the slit is open, the controller 101 controls the slit forming unit 54 based on the control contents determined in Step 42 to close the slit. Note that if Step 44 is performed, timing of execution of Step 43 and that of Step 44 are arbitrary.

[Sixth Operational Example: FIG. 9]

The sixth operational example explains a case of presenting the kind (visible, infrared) of the background illumination light that is currently used. The sixth operational example can be applied to a case in which the background illumination system 20 is provided with both a visible background light source and an infrared background light source.

(Step 51: Instruction for Setting Kind of Background Illumination Light)

As a control instruction, an instruction is issued for outputting background illumination light of a desired kind. This control instruction is an instruction for irradiating the eye E with background illumination light of the desired kind when background illumination light is not irradiated, or an instruction for switching from one state in which background illumination light is irradiated to another state in which background illumination light of another kind is irradiated. This control instruction is issued by use of the operating unit 103 or by the controller 101.

(Step 52: Control of Background Light Source)

The controller 101 controls the visible background light source 20*a* and/or the infrared background light source 20*b* so as to output background illumination light of the kind instructed in Step 51. If the control instruction in the Step 51 is issued when both the visible background light source 20*a* and the infrared background light source 20*b* are turned off, the controller 101 turns on the background light source corresponding to the kind instructed (that is, the visible background light source 20*a* or the infrared background light source 20*b*). If the control instruction in the Step 51 is issued when one of the visible background light source 20*a* and the infrared background light source 20*b* (for example, the visible background light source 20*a*) is turned off, the controller 101 turns off this background light source (for example, the visible background light source 20*a*) and turns on the other background light source (for example, the infrared background light source 20*b*).

(Step 53: Presenting Kind of Background Illumination Light)

The controller 101 displays, on the display 102, information indicating the kind (visible, infrared) of the background illumination light instructed to irradiate in Step 51. Here, timing of execution of Step 52 and that of Step 53 are arbitrary.

In another example of processing, the controller 101 displays, on the display 102, information indicating the kind (visible, infrared) of the background light source turned on in Step 52. In this case, Step 53 is performed after Step 52.

Actions and Effects

Actions and effects of slit lamp microscopes according to embodiments are explained.

A slit lamp microscope according to an embodiment includes a main illumination system, a background illumination system, an observation system and a controller.

The main illumination system (illumination system 8) includes a first light source unit (light source 51) that outputs first light (illumination light) and a slit forming unit (slit forming unit 54) that forms a slit whose width is variable. The main illumination system illuminates an eye with the first light having passed through the slit.

The background illumination system (background illumination system 20) includes a second light source unit (background light source) that outputs second light (background illumination light), and illuminates, with the second light, a peripheral area of an area of the eye irradiated with the first light.

The observation system (observation system 6) includes an eyepiece lens (eyepiece lens 37), an imaging device (imaging device 13), and a group of optical elements. The group of optical elements guides reflected light of the first light and reflected light of the second light from the eye to the eyepiece lens and the imaging device.

The controller (controller 101) controls the main illumination system (illumination system 8) and the second light source unit (background light source) in an interlocking fashion.

According to the slit lamp microscope thus configured, it is possible to interlockingly control irradiation of slit light by the main illumination system and irradiation of background illumination light by the background illumination system.

The controller (controller 101) interlockingly may be configured to control the first light source unit (light source 51) in the main illumination system (illumination system 8) and the second light source unit (background light source).

With this, it is possible to interlockingly control an irradiation state of the slit light (brightness of the slit light) due to the first light source unit and an irradiation state of the background illumination light. Examples of such control linkage include the aforementioned first to third operational examples.

When received a control instruction to the second light source unit (background light source), the controller (controller 101) is capable of interlockingly controlling the first light source unit (light source 51) and the second light source unit (background light source) based on contents of the control instruction.

With this, it is possible to interlockingly control an irradiation state of the slit light and an irradiation state of the background illumination light in response to a control instruction for an irradiation state of background illumination light. Examples of such control linkage include the aforementioned first and second operational examples.

If the first light source unit (light source 51) includes a first visible light source (light source 51) that outputs first visible light as the first light, and the second light source unit (background light source) includes a second visible light source (visible background light source 20a) that outputs second visible light as the second light, the controller (controller 101) may be configured to perform the following interlocking control.

When an instruction for changing intensity of the second visible light is received as the control instruction, the controller (controller 101) controls the second visible light source (visible background light source 20a) so as to change the intensity of the second visible light by a first change amount corresponding to this instruction and controls the first visible light source (light source 51) so as to change intensity of the first visible light by a second change amount corresponding to the first change amount.

According to this interlocking control, the brightness of the slit light is automatically adjusted according to adjustment of the brightness of the background illumination light, thereby reducing the amount of word by the user. Examples of such control linkage include the aforementioned first operational example.

If the first light source unit (light source 51) includes a first visible light source (light source 51) that outputs first visible light as the first light, and the second light source unit (background light source) includes a second visible light source (visible background light source 20a) that outputs second visible light as the second light and an infrared light source (infrared background light source 20b) that outputs infrared light as the second light, the controller (controller 101) may be configured to perform the following interlocking control.

The controller (controller 101) selectively turns on the second visible light source (visible background light source 20a) and the infrared light source (infrared background light source 20b). When an instruction for turning on the infrared light source (infrared background light source 20b) is received as the control instruction, the controller (controller 101) controls the second light source unit (background light source) so as to turn on the infrared light source (infrared background light source 20b) and controls the first visible light source (light source 51) so as to stop output of the first visible light.

According to this interlocking control, it is possible to automatically turn off unnecessary illumination light (slit light) when use of infrared background illumination light is instructed, for example, at the time of commencing observation of meibomian glands. Examples of such control linkage include the aforementioned second operational example.

When a control instruction to the first light source unit (light source 51) is received, the controller (controller 101) is capable of interlockingly controlling the first light source unit (light source 51) and the second light source unit (background light source) based on contents of the control instruction.

With this, it is possible to interlockingly control an irradiation state of the slit light and an irradiation state of the background illumination light in response to a control instruction for an irradiation state of slit light. Examples of such control linkage include the aforementioned third operational example.

If the first light source unit (light source 51) includes a first visible light source (light source 51) that outputs first visible light as the first light, and the second light source unit (background light source) includes a second visible light source (visible background light source 20a) that outputs second visible light as the second light, the controller (controller 101) may be configured to perform the following interlocking control.

When an instruction for changing intensity of the first visible light is received as the control instruction, the controller (controller 101) controls the first visible light source (light source 51) so as to change the intensity of the first visible light by a first change amount corresponding to the instruction and controls the second visible light source (visible background light source 20a) so as to change intensity of the second visible light by a second change amount corresponding to the first change amount.

According to this interlocking control, the brightness of the background illumination light is automatically adjusted according to adjustment of the brightness of the slit light, thereby reducing the amount of word by the user. Examples of such control linkage include the aforementioned third operational example.

The controller (controller 101) interlockingly may be configured to control the slit forming unit (slit forming unit 54) in the main illumination system (illumination system 8) and the second light source unit (background light source).

With this, it is possible to interlockingly control an irradiation state of the slit light (slit width) due to the slit forming unit and an irradiation state of the background illumination light. Examples of such control linkage include the aforementioned fourth and fifth operational examples.

If the first light source unit (light source 51) includes a first visible light source (light source 51) that outputs first visible light as the first light, and the second light source unit (background light source) includes a second visible light source (visible background light source 20a) that outputs second visible light as the second light, the controller (controller 101) may be configured to perform the following interlocking control.

When a control instruction for changing width of the slit is received, the controller (controller 101) controls the slit forming unit (slit forming unit 54) so as to change the width of the slit by a first change amount corresponding to the instruction and controls the second visible light source (visible background light source 20a) so as to change intensity of the second visible light by a second change amount corresponding to the first change amount.

According to this interlocking control, the brightness of the background illumination light is automatically adjusted according to adjustment of the slit width, thereby reducing the amount of word by the user. Examples of such control linkage include the aforementioned fourth operational example.

When controlling the slit forming unit (slit forming unit 54) to increase the width of the slit to a value equal to or larger than a preset threshold, the controller (controller 101) turns off the second visible light source (visible background light source 20a).

According to this interlocking control, it is possible to automatically turn off unnecessary background illumination light in response to increase of the slit width to a value equal to or larger than a threshold, thereby reducing the amount of word by the user. Examples of such control linkage include the aforementioned fourth operational example.

If the first light source unit (light source 51) includes a first visible light source (light source 51) that outputs first visible light as the first light, and the second light source unit (background light source) includes a second visible light source (visible background light source 20a) that outputs second visible light as the second light and an infrared light source (infrared background light source 20b) that outputs infrared light as the second light, the controller (controller 101) may be configured to perform the following interlocking control.

The controller (controller 101) selectively turns on the second visible light source (visible background light source 20a) and the infrared light source (infrared background light source 20b). When an instruction for turning on the infrared light source (infrared background light source 20b) is received as the control instruction, the controller (controller 101) controls the second light source unit (background light source) so as to turn on the infrared light source (infrared background light source 20b) and controls the slit forming unit (slit forming unit 54) so as to close the slit.

According to this interlocking control, it is possible to automatically stop irradiation of the eye with unnecessary illumination light (slit light) when use of infrared background illumination light is instructed, for example, at the time of commencing observation of meibomian glands. Examples of such control linkage include the aforementioned fifth operational example.

A slit lamp microscope according to an embodiment may include an operating unit (operating unit 103) for inputting a control instruction.

With this, it is possible to perform the interlocking controls described above in response to a control instruction by hand.

If the second light source unit (background light source) includes a visible light source (visible background light source 20a) that outputs visible light as the second light and an infrared light source (infrared background light source 20b) that outputs infrared light as the second light, the controller (controller 101) may be configured to perform the following interlocking control.

The controller (controller 101) selectively turns on the visible light source (visible background light source 20a) and the infrared light source (infrared background light source 20b). Further, the controller (controller 101) displays, on a display means (display 102), information indicating which of the visible light source (visible background light source 20a) and the infrared light source (infrared background light source 20b) is being turned on.

With this, the user can become aware of the type (visible, infrared) of background illumination light being used.

Here, the information displayed may include not only the kind of background illumination light but also information indicating the intensity (brightness) thereof.

The display means may be included in the slit lamp microscope of the embodiment and may be an external display device. The display means is not necessarily a display device (LCD etc.). For example, one or more light emitting members (LEDs etc.), whose operating state is controlled by the controller (controller 101) according to kinds and/or intensity of background illumination light, may be used as the display means.

The configurations of the above embodiments are no more than examples for implementing the present invention. A person attempting to implement the present invention is allowed any modification (addition, omission, replacement, and the like) within the scope of the present invention.

EXPLANATION OF SYMBOLS

1 Slit lamp microscope
6 Observation system
8 Illumination system
13 Imaging device
20 Background illumination system
20a Visible background light source
20b Infrared background light source
37 Eyepiece lens
51 Light source
54 Slit forming unit
100 Computer
101 Controller
102 Display
103 operating unit
E eye

What is claimed is:

1. A slit lamp microscope, comprising:
a main illumination system that includes a first light source unit that outputs first light and a slit forming unit that forms a slit with changeable width, and illuminates an eye with the first light having passed through the slit;
a background illumination system that includes a second light source unit that outputs second light, and illuminates, with the second light, a peripheral area of an area of the eye irradiated with the first light;
an observation system that includes an eyepiece lens, an imaging device, and a group of optical elements that guides reflected light of the first light and reflected light of the second light from the eye to the eyepiece lens and the imaging device; and
a controller that interlockingly controls the main illumination system and the second light source unit, wherein
the controller interlockingly controls the first light source unit and the second light source unit,
the controller receives a control instruction to the second light source unit and interlockingly controls the first light source unit and the second light source unit based on contents of the control instruction,
the first light source unit includes a first visible light source that outputs first visible light as the first light,
the second light source unit includes a second visible light source that outputs second visible light as the second light and an infrared light source that outputs infrared light as the second light, and
the controller selectively turns on the second visible light source and the infrared light source, and when an instruction for turning on the infrared light source is received as the control instruction, the controller controls the second light source unit so as to turn on the infrared light source and controls the first visible light source so as to stop output of the first visible light.

2. The slit lamp microscope of claim 1, further comprising an operating unit for inputting the control instruction.

3. A slit lamp microscope, comprising:
a main illumination system that includes a first light source unit that outputs first light and a slit forming unit that forms a slit with changeable width, and illuminates an eye with the first light having passed through the slit;
a background illumination system that includes a second light source unit that outputs second light, and illuminates, with the second light, a peripheral area of an area of the eye irradiated with the first light;
an observation system that includes an eyepiece lens, an imaging device, and a group of optical elements that guides reflected light of the first light and reflected light of the second light from the eye to the eyepiece lens and the imaging device; and
a controller that interlockingly controls the main illumination system and the second light source unit, wherein
the controller interlockingly controls the slit forming unit and the second light source unit,
the first light source unit includes a first visible light source that outputs first visible light as the first light,
the second light source unit includes a second visible light source that outputs second visible light as the second light, and
when a control instruction for changing the width of the slit is received, the controller controls the slit forming unit so as to change the width of the slit by a first change amount corresponding to the control instruction and controls the second visible light source so as to change intensity of the second visible light by a second change amount corresponding to the first change amount.

4. The slit lamp microscope of claim 3, wherein when the controller controls the slit forming unit to increase the width of the slit to a value equal to or larger than a preset threshold, the controller turns off the second visible light source.

5. The slit lamp microscope of claim 3, further comprising an operating unit for inputting the control instruction.

6. A slit lamp microscope, comprising:
a main illumination system that includes a first light source unit that outputs first light and a slit forming unit that forms a slit with changeable width, and illuminates an eye with the first light having passed through the slit;
a background illumination system that includes a second light source unit that outputs second light, and illuminates, with the second light, a peripheral area of an area of the eye irradiated with the first light;
an observation system that includes an eyepiece lens, an imaging device, and a group of optical elements that guides reflected light of the first light and reflected light of the second light from the eye to the eyepiece lens and the imaging device; and
a controller that interlockingly controls the main illumination system and the second light source unit, wherein
the controller interlockingly controls the slit forming unit and the second light source unit,
the first light source unit includes a first visible light source that outputs first visible light as the first light,
the second light source unit includes a second visible light source that outputs second visible light as the second light and an infrared light source that outputs infrared light as the second light, and
the controller selectively turns on the second visible light source and the infrared light source, and when a control instruction for turning on the infrared light source is received, the controller controls the second light source unit so as to turn on the infrared light source and controls the slit forming unit so as to close the slit.

7. The slit lamp microscope of claim 6, further comprising an operating unit for inputting the control instruction.

* * * * *